(12) United States Patent
Tan et al.

(10) Patent No.: US 8,858,770 B2
(45) Date of Patent: Oct. 14, 2014

(54) PLASTIC MICROFLUIDIC SEPARATION AND DETECTION PLATFORMS

(75) Inventors: Eugene Tan, Arlington, MA (US); Cheuk Wai Kan, Boston, MA (US); Heung Chuan Lam, Newton, MA (US)

(73) Assignee: NetBio, Inc., Waltham, MA (US)

( * ) Notice: Subject to any disclaimer, the term of this patent is extended or adjusted under 35 U.S.C. 154(b) by 1189 days.

(21) Appl. No.: 12/080,745

(22) Filed: Apr. 4, 2008

(65) Prior Publication Data
US 2009/0020427 A1    Jan. 22, 2009

Related U.S. Application Data

(60) Provisional application No. 61/028,073, filed on Feb. 12, 2008, provisional application No. 60/921,802, filed on Apr. 4, 2007, provisional application No. 60/964,502, filed on Aug. 13, 2007.

(51) Int. Cl.
| | | |
|---|---|---|
| *G01N 27/447* | (2006.01) | |
| *B01L 3/00* | (2006.01) | |
| *G01N 21/64* | (2006.01) | |
| *B01L 7/00* | (2006.01) | |

(52) U.S. Cl.
CPC ........ *G01N 21/6486* (2013.01); *G01N 21/6428* (2013.01); *G01N 27/44782* (2013.01); *B01L 2200/0684* (2013.01); *B01L 2200/10* (2013.01); *B01L 2300/0816* (2013.01); *G01N 21/6452* (2013.01); *B01L 7/52* (2013.01); *G01N 27/44791* (2013.01); *B01L 2300/069* (2013.01); *B01L 2300/0887* (2013.01); *B01L 2400/0421* (2013.01); *B01L 3/502753* (2013.01); *G01N 27/44726* (2013.01)
USPC ....... 204/452; 204/603; 422/68.1; 422/82.01; 435/287.1

(58) Field of Classification Search
USPC ................. 204/600–645, 450–472
See application file for complete search history.

(56) References Cited

U.S. PATENT DOCUMENTS

| | | | | |
|---|---|---|---|---|
| 5,858,188 A | * | 1/1999 | Soane et al. ............... | 204/454 |
| 6,207,031 B1 | | 3/2001 | Adourian et al. | |
| 6,485,625 B1 | * | 11/2002 | Simpson et al. ............ | 204/601 |
| 6,787,016 B2 | * | 9/2004 | Tan et al. ................... | 204/455 |
| 6,800,438 B2 | * | 10/2004 | Noolandi et al. ........... | 435/6.11 |
| 6,827,906 B1 | | 12/2004 | Bjornson et al. | |

(Continued)

FOREIGN PATENT DOCUMENTS

| | | | |
|---|---|---|---|
| EP | WO02/35223 | * | 5/2002 |
| JP | 2003-194775 | | 7/2003 |

(Continued)

OTHER PUBLICATIONS

Gedecke et al. (Electrophoresis, 2004, 25, 1678-1686).*

(Continued)

*Primary Examiner* — Jennifer Dieterle
(74) *Attorney, Agent, or Firm* — Proskauer Rose LLP

(57) ABSTRACT

Plastic electrophoresis separation chips are provided comprising a plurality of microfluidic channels and a detection window, where the detection window comprises a thin plastic; and the detection window comprises a detection region of each microfluidic channel. Such chips can be bonded to a support provided an aperture is provided in the support to allow detection of samples in the electrophoresis chip at the thin plastic detection window. Further, methods for electrophoretically separating and detecting a plurality of samples on the plastic electrophoresis separation chip are described.

25 Claims, 16 Drawing Sheets

(56) References Cited

U.S. PATENT DOCUMENTS

| | | | |
|---|---|---|---|
| 6,991,713 B2 * | 1/2006 | Adourian et al. | 204/453 |
| 7,150,815 B2 | 12/2006 | Ashmead et al. | |
| 7,708,870 B2 | 5/2010 | Tabuchi et al. | |
| 2002/0056639 A1 | 5/2002 | Lackritz et al. | |
| 2002/0155485 A1 | 10/2002 | Kao | |
| 2003/0089605 A1 | 5/2003 | Timperman | |
| 2003/0209436 A1 * | 11/2003 | Nordman et al. | 204/452 |
| 2004/0175299 A1 * | 9/2004 | Belenky et al. | 422/101 |
| 2004/0178071 A1 * | 9/2004 | Harrison et al. | 204/450 |
| 2005/0109621 A1 * | 5/2005 | Hauser et al. | 204/451 |
| 2005/0135655 A1 * | 6/2005 | Kopf-Sill et al. | 382/100 |
| 2006/0141446 A1 * | 6/2006 | Murphy et al. | 435/4 |
| 2006/0207880 A1 * | 9/2006 | Joyce et al. | 204/451 |
| 2006/0266649 A1 | 11/2006 | Nakamura et al. | |

FOREIGN PATENT DOCUMENTS

| | | |
|---|---|---|
| JP | 2004-523728 | 3/2004 |
| JP | 2005-509872 | 4/2005 |
| JP | 2007-506092 | 3/2007 |
| WO | 9919717 A | 4/1999 |
| WO | 2006-124842 A | 11/2006 |

OTHER PUBLICATIONS

Bhattacharyya et al. (Analytical Chemistry, vol. 78, No. 3, Feb. 1, 2006, published on web Dec. 23, 2005).*
Piruska et al. (Lab Chip, 2005, 5, 1348-1354).*
Shadpour et al. (Journal of Chromatography A, 1111, available online Oct. 5, 2005, 238-251).*
Zeonor website downloaded Jan. 27, 2012, product specification sheet.*

* cited by examiner

PLASTIC MICROFLUIDIC SEPARATION AND DETECTION PLATFORMS

CROSS-REFERENCE TO RELATED APPLICATIONS

This application claims the benefit of the filing date, under 35 U.S.C. §119 (e), of U.S. Provisional Application Ser. No. 60/921,802, filed 4 Apr. 2007; and U.S. Provisional Application Ser. No. 60/964,502 filed 13 Aug. 2007, and U.S. Provisional Application Ser. No. 61/028,073, filed Feb. 12, 2008, each of which is hereby incorporated by reference in its entirety. This application also incorporates by reference, in their entirety two US applications filed on even date herewith, application Ser. No. 12/080,746, now issued as U.S. Pat. No. 8,425,861, entitled "METHODS FOR RAPID MULTIPLEXED AMPLIFICATION OF TARGET NUCLEIC ACIDS"; and application Ser. No. 12/080,751, now issued as U.S. Pat. No. 8,018,593, entitled "INTEGRATED NUCLEIC ACID ANALYSIS."

FIELD OF THE INVENTION

This invention is in the field of nucleic acid sequencing and fragment sizing by electrophoresis with detection by laser-induced fluorescence. The analysis is performed on plastic electrophoresis chips.

BACKGROUND OF THE INVENTION

Since the advent of DNA sequencing technologies in the 1970's (Maxam & Gilbert, 1977, *Proc Natl Acad Sci USA* 74: 560-564; Sanger et al., 1977, *Proc Natl Acad Sci USA* 74: 5463-5467), a wide range of applications making use of these technologies has developed. In parallel, increasingly sophisticated instrumentation to perform DNA sequencing has been introduced. For example, in 1986, Applied Biosystems commercialized an automated DNA sequencer based on separation of DNA fragments generated by the Sanger sequencing method; DNA fragments were labeled with a set of four fluorescent dyes and separated by capillary electrophoresis (Smith et al., 1986, *Nature* 321: 674-679). As a result, Sanger sequencing has been the most widely utilized sequencing technology for the last three decades.

More recently, a variety of new sequencing technologies and related instrumentation have been and continue to be developed. Termed "next generation" methods (reviewed in Metzker, 2005, *Genome Research* 15: 1767-1776), these chemistries include pyrosequencing, sequencing-by-ligation, and single molecule sequencing. A major goal driving research into next generation sequencing technologies is to perform high-throughput genomic sequencing in general, and to reduce the cost of obtaining a complete genome sequence in particular. Although the cost per base pair of next-generation technologies may be less in some cases than that of Sanger sequencing, all these methods (including Sanger) are costly and require substantial time, labor, and laboratory equipment.

The current emphasis on obtaining very large amounts of sequence data from a given genome does not negate the value of obtaining relatively small amounts of genomic sequence quickly. For example, many common human diseases can be diagnosed based on less than 1000 base pairs of DNA sequences, orders of magnitude less than required to generate a complete human genome. Similarly, precise determination of the sizes of sets of less than 20 specific DNA fragments generated by short tandem repeat analysis is sufficient to identify a given individual.

There is an unmet need for the development of instruments and technologies that would permit focused nucleic acid analysis, defined as the rapid identification (by nucleic acid sequencing or fragment sizing) of a subset of a given human, animal or pathogen genome. Focused nucleic acid analysis will enable end-users to make near-real time clinical, forensic, or other decisions. Depending on the application, focused nucleic acid analysis may be performed in a variety of settings, including hospital laboratories, physician's offices, the bedside, or, in the case of forensic or environmental applications, in the field.

With respect to nucleic acid (DNA and RNA) sequencing, clinical applications include diagnosis of bacterial, fungal, and viral diseases (including the determination of drug resistance profiles of the organisms), cancer (including the determination of responsiveness to chemotherapeutic regimens), and inherited and other common diseases (including the determination of responsiveness to medications). Focused nucleic acid sequencing is also well suited for pharmacogenomic analysis and certain forensic applications (including, for example, mitochondrial DNA sequencing).

With respect to nucleic acid fragment sizing, focused nucleic acid analysis can be utilized in forensic and clinical applications. For example, one type of human identification is based on a short tandem repeat (STR) analysis (Edwards et al., 1991, *Am J Hum Genet* 49(4)746:756). In STR analysis, a series of primers are utilized to amplify certain genomic regions that contain variable numbers of certain short tandem repeats. The sizes of the resulting bands are determined by nucleic acid fragment sizing (typically using capillary electrophoresis), and the size of each member of the set of STR alleles uniquely identifies an individual. STR typing has become the worldwide standard for human forensic genetic identification and is the only biometric technology that allows identification of an individual as well as genetic relatives of that individual. In clinical applications, nucleic acid fragment sizing can be used to diagnose a given disorder (e.g., by searching for a characteristic deletion or insertion, or determining the size of nucleotide repeat regions as in Friedreich ataxia (Pandolfo, M., 2006, *Methods Mol. Med* 126: 197-216). Fragment sizing is also useful for the identification of infectious agents; DNA fingerprinting can be utilized in pathogen diagnosis.

The applications of focused nucleic acid analysis are not limited to those discussed above. Focused nucleic acid analysis can be utilized to identify biological weapons agents in clinical and environmental samples by both sequencing and fragment sizing. Veterinary and food testing applications also mirror those described above. Veterinary identification applications such as racehorse breeding and tracking, livestock breeding, and pet identification also are within the scope of the uses of the disclosed invention. Research applications of focused nucleic acid analysis are numerous. In short, focused nucleic acid analysis has the potential to dramatically transform several industries.

The existing high throughput capillary-based sequencers and the next generation sequencers are not capable of performing focused nucleic acid analysis in a timely and cost-effective fashion. The economies of scale sought by those technologies are driven by reducing the costs of obtaining and analyzing very large amounts of sequence data. For instruments and systems capable of focused nucleic acid analysis to make their way into routine use, they should be designed to possess certain "ideal" properties and features. In particular, the instruments and systems should generate results rapidly (ideally within minutes) to allow the generation of actionable data as quickly as possible. They should be easy to operate and reagents and consumables should be inexpensive. In addition, for some applications it is useful for nucleic acid separations to be performed in disposables; this dramatically reduces the possibility of sample contamination. To achieve these properties, polymer-based biochips are better suited as separation substrates than other materials such as glass and silicon.

An attempt to achieve DNA fragment sizing on plastic chips was reported by McCormick (*Anal Chem* 69(14):2626 1997) showing the separation of HaeIII restriction fragments of ΦX174 RF DNA. The separations were performed with single samples in single lane chips, but nevertheless exhibited poor resolution separations and poor sensitivity. Furthermore, the system was only able to detect emission from a single fluorophore. Sassi (*J Chromatogr A*, 894(1-2):203 2000) reported the use of acrylic chips consisting of 16 fluidically isolated separation lanes for STR sizing, but this approach also showed poor resolving power and low sensitivity. This low system sensitivity prevented the detection of allelic ladders (internal sizing standards strictly required in forensic analysis) when performing simultaneous 16-lane separation and detection. The use of a 2 Hz scanning rate, representing an attempt to increase the signal to noise ratio of the system, caused degradation of both resolving power and precision. Finally, the system was only able to detect emission from a single fluorophore. Shi (*Electrophoresis* 24(19-20): 3371 2003 and Shi, 2006, *Electrophoresis* 27(10):3703) reported 2- and 4-color separation and detection in single sample, single lane plastic separation devices. While the 4.5 cm channel was reported to provide single base resolution, in actuality the resolution is poor as evidenced by the appearance of alleles spaced one base pair apart (the peak-to-valley ratio of the TH01 9.3 and 10 alleles approaches one). Devices with longer separation channels (6, 10 and 18-cm) were used in this study to achieve higher resolution for analysis compared to the 4.5 cm devices. Resolution of the 10 and 18-cm long devices were limited as the devices delaminated when sieving matrices compositions optimized for resolution were used.

In practice, plastics have been found to present several major obstacles for use in biochips designed for nucleic acid sequencing and fragment sizing. Autofluorescence of plastic materials interferes with the detection of wavelengths in the visible range of 450 to 800 nm (Puriska, 2005, *Lab Chip* 5(12):1348; Wabuyele, 2001 *Electrophoresis* 22(18):3939-48; Hawkins and Yager 2003 *Lab Chip*, 3(4): 248-52).

These wavelengths are used in commercial kits for Sanger sequencing and STR sizing. Furthermore, existing plastic devices have low bonding strengths to commonly-used substrates and poor performance results with commonly-used sieving matrices. Finally, inner surfaces of the channel interact with sieving matrices and the DNA samples resulting in poor resolution due to electroosmotic flow and DNA-to-wall interactions (Kan, 2004, *Electrophoresis* 25(21-22):3564).

Accordingly, there is a substantial unmet need for an inexpensive, multi-lane plastic biochip capable of performing focused nucleic acid analysis at high resolution and with a high signal to noise ratio.

SUMMARY OF THE INVENTION

This invention provides inexpensive, multi-lane plastic biochips capable of performing focused nucleic acid analysis at high resolution and with a high signal to noise ratio and methods of using such chips.

In a first aspect, the invention provides plastic separation chips, and in particular electrophoresis chips comprising an anode portion, a cathode portion, and a center portion between the anode and cathode portions, wherein the cathode portion comprises at least one first via; the anode portion comprises at least one second via; and the center portion comprises a plurality of microfluidic channels and a detection window, each microfluidic channel having a separation region and a detection region; wherein each microfluidic channel is in fluid communication with at least one first via and at least one second via; wherein the plurality of microfluidic channels are in substantially the same plane; the plurality of microfluidic channels do not intersect one another within the center portion; the detection window comprises a thin plastic; and the detection window comprises the detection region of each microfluidic channel. The portions of the chip outside of the detection region can of the same thickness, or of a thickness that larger than that of the detection region.

In a second aspect, the invention provides devices comprising a support having a top and bottom surface, comprising an anode portion, a cathode portion, and a center portion between the anode and cathode portions, wherein the center portion comprises an aperture at the detection window, the anode portion comprises the at least one anode well, and the cathode portion comprises the at least one cathode well; the apparatus further comprising a chip according to the first aspect, having a top and bottom surface, wherein the top surface of the chip is in contact with the bottom surface of the support, the microfluidic channels are in fluid communication with the cathode and anode wells through the vias; and the chip is fixedly attached to the support.

In a third aspect, the invention provides methods for electrophoretically separating and detecting a plurality of samples simultaneously, comprising providing a plurality of samples into each of a plurality of microfluidic channels on a microchip according to the first aspect; applying an electric potential across the plurality of microfluidic channels to inject samples into the separation channel and to separate detectable species comprising each of the plurality of analysis samples; and detecting each of the detectable species comprising the plurality of separated samples at the detection window.

Specific preferred embodiments of the present invention will become evident from the following more detailed description of certain preferred embodiments and the claims.

DETAILED DESCRIPTION OF THE INVENTION

Figure 1:
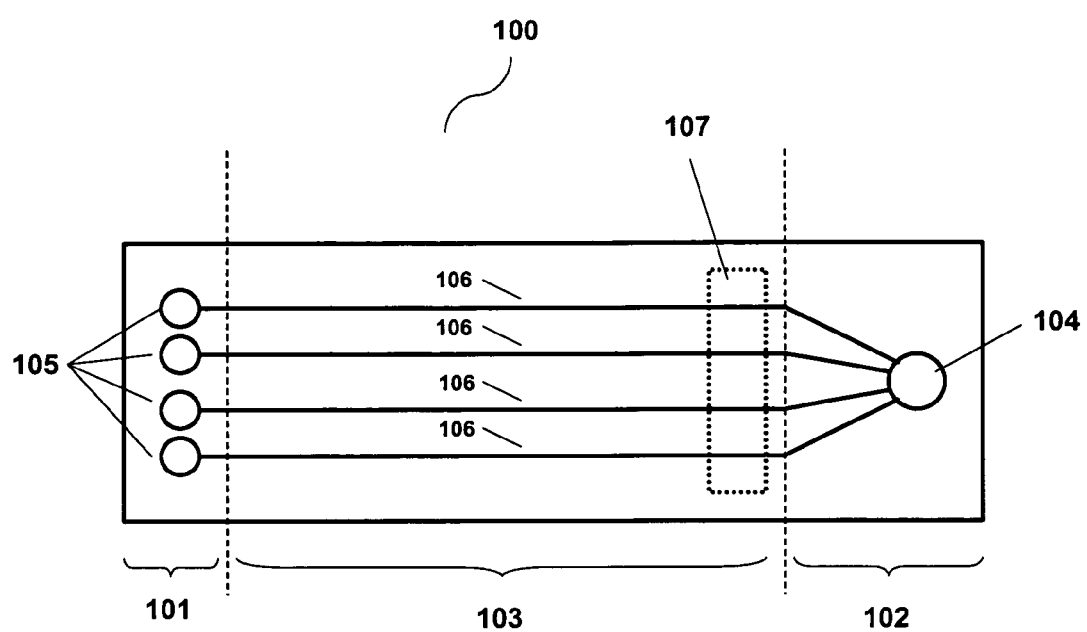
FIG. 1 illustrates a microfluidic separation and detection chip according to the various embodiments of the invention.

The invention provides plastic separation chips that are capable of detecting separation of nucleic acid species differing in size by about 1 basepair, and at concentration levels of at least 1.0 ng of DNA template.

The lowest level of sample to be analyzed for STR analysis consists of a nucleic acid template with less than 800 copies, less than 400 copies, less than 200 copies, less than 100 copies, less than 50 copies, less than 30 copies, less than 10 copies or 1 copy of nucleic acid template prior to the multiplexed PCR reaction. The lowest concentration sample to be analyzed for Sequencing consists of a nucleic acid template with less than 0.5 pmole, less than 0.1 pmole, less than 0.01 pmole as input to the Sanger sequencing reaction.

The phrase "injection channel" as used herein, means an intersecting channel that permits introduction of a sample into the microfluidic channel with which it intersects. The intersecting channel can be in a single cross-channel, a single T-junction, or an offset double-T junction configuration.

The phrase "fluid communication" as used herein, refers to two chambers, or other components or regions containing a fluid, connected together so that a fluid can flow between the two chambers, components, or regions. Therefore, two chambers which are in "fluid communication" can, for example, be connected together by a microfluidic channel between the two chambers, such that a fluid can flow freely between the two chambers. Such microfluidic channels can optionally include one or more valves therein which can be closed or occluded, in order to block and/or otherwise control fluid communication between the chambers.

The phrase "fluorescent dye" as used herein, means the dye, upon excitation with a light source, emits light having a wavelength of 380-850 nm. Preferably, the dye emits light having a wavelength between about 450-800 nm; more preferably, the dye emits light having a wavelength between about 495-775 nm.

The term "autofluorescence" as used herein, means fluorescence produced by substances other than the fluorophore of interest under light irradiation.

The phrase "essentially does not fluoresce" as used herein, means the background fluorescence signal (for example, between about 380-850 nm; 400-800 nm; 450-800 nm; 500-800 nm, or 495-775 nm) from the referenced object (e.g., solid or solution) when subjected to light irradiation (e.g., at one or more wavelengths between about 350-500 nm, 400-500 nm, or 450-500 nm; in particular, 488 nm; laser irradiation) has a background level that is lower than that from conventional glass microfluidic devices which consist of borofloat glass of 0.7 mm thick.

The term "norbornene based polymers" as used herein means a polymer prepared from at least one monomer comprising a norbornene moiety where the norbornene-containing monomers are polymerized according to ring-opening metathesis polymerization according to methods known to those skilled in the art (see, for example, U.S. Pat. Nos. 4,945,135; 5,198,511; 5,312,940; and 5,342,909).

The term "poly(methyl methacrylate) or "PMMA," as used herein, means the synthetic polymers of methyl methacrylate, including but not limited to, those sold under the tradenames Plexiglas™, Limacryl™, R-Cast™, Perspex™, Plazcryl™, Acrylex™, ACrylite™, ACrylplast™, Altuglas™, Polycast™ and Lucite™, as well as those polymers described in U.S. Pat. Nos. 5,561,208, 5,462,995, and 5,334,424, each of which are hereby incorporated by reference.

The term "polycarbonate" as used herein means a polyester of carbonic acid and glycol or a divalent phenol. Examples of such glycols or divalent phenols are p-xylene glycol, 2,2-bis (4-oxyphenyl)propane, bis(4-oxyphenyl)methane, 1,1-bis(4-oxyphenyl)ethane, 1,1-bis(oxyphenyl)butane, 1,1-bis(oxyphenyl)cyclohexane, 2,2-bis(oxyphenyl)butane, and mixtures thereof, including but not limited to, those sold under the tradenames Calibre™, Makrolon™, Panlite™, Makroclear™, Cyrolon™, Lexan™ and Tuffak™.

As used herein the term "nucleic acid" is intended to encompass single- and double-stranded DNA and RNA, as well as any and all forms of alternative nucleic acid containing modified bases, sugars, and backbones. The term "nucleic acid" thus will be understood to include, but not be limited to, single- or double-stranded DNA or RNA (and forms thereof that can be partially single-stranded or partially double-stranded), cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup, 1997, Biochemistry 36:8692-8698), and benzylphosphonate linkages, as discussed in U.S. Pat. No. 6,664,057; see also OLIGONUCLEOTIDES AND ANALOGUES, A PRACTICAL APPROACH, edited by F. Eckstein, IRL Press at Oxford University Press (1991); *Antisense Strategies*, Annals of the New York Academy of Sciences, Volume 600, Eds. Baserga and Denhardt (NYAS 1992); Milligan, 1993, *J. Med. Chem.* 36:1923-1937; Antisense Research and Applications (1993, CRC Press). The nucleic acids herein can be extracted from cells or synthetically prepared according to any means known to those skilled in the art; for example, the nucleic acids can be chemically synthesized or transcribed or reverse transcribed from cDNA or mRNA, among other sources.

The term "via" as used herein means a through-hole formed in a solid material to allow fluidic connection between the top and bottom surfaces of the material.

An exemplary electrophoresis chip according to various embodiments of the invention is shown in FIG. 1. The chip (100) comprises an anode portion (101), a cathode portion (102), and a center portion (103) between the anode and cathode portions. The cathode portion comprises at least one first via (104) and the anode portion comprises at least one second via (105). The center portion comprises a plurality of microfluidic channels (106) and a detection window (107), each microfluidic channel having a separation region and a detection region; wherein each microfluidic channel is in fluid communication with at least one first via and at least one second via. The plurality of microfluidic channels are substantially in the same plane and do not intersect one another within the center portion. Each microfluidic channel has a region in where excitation and/or detection of the sample can take place. The area in which encompasses the excitation and detection regions of the plurality of microfluidic channels is known as the detection window, and this window comprises a thin plastic.

The phrase "thin plastic" as used herein, means the referenced material comprises a plastic having a thickness of (its smallest dimension) less than 1 mm, less than 750 µm, less than 650 µm, less than 500 µm, less than 400 µm, less than 300 µm, less than 200 µm, or less than 100 µm; or the referenced material comprises a plastic having a thickness ranging from 25-2000 µm, 25-1000, 25-750 µm, 25-500 µm, 25-400 µm, 25-300 µm, or 25-200 µm. Although the chip is designed to be thin in the detection window, portions of the chip outside of the detection region can be of the same thickness, or of a thickness that is larger than that of the detection region.

The chip of FIG. 1 is shown for the sake of illustration as having four microfluidic channels, however such disclosure is not intended to be limiting, rather, one skilled in the art will readily recognize that the chip can contain alternate numbers of microfluidic channels (infra) including chips with one channel and chips with two or more channels. The term "plurality" as used herein, means two or more, four or more, eight or more, 16 or more, 32 or more, 48 or more, 64 or more, 96 or more, 128 or more, 256 or more, 384 or more, 512 or more, or 1024 or more; or 2-4, 2-8, 2-16, 2-32, 2-48, 2-64, 2-96, 2-128, 2-384, 2-512, 2-1024 microfluidic channels.

Figure 3:
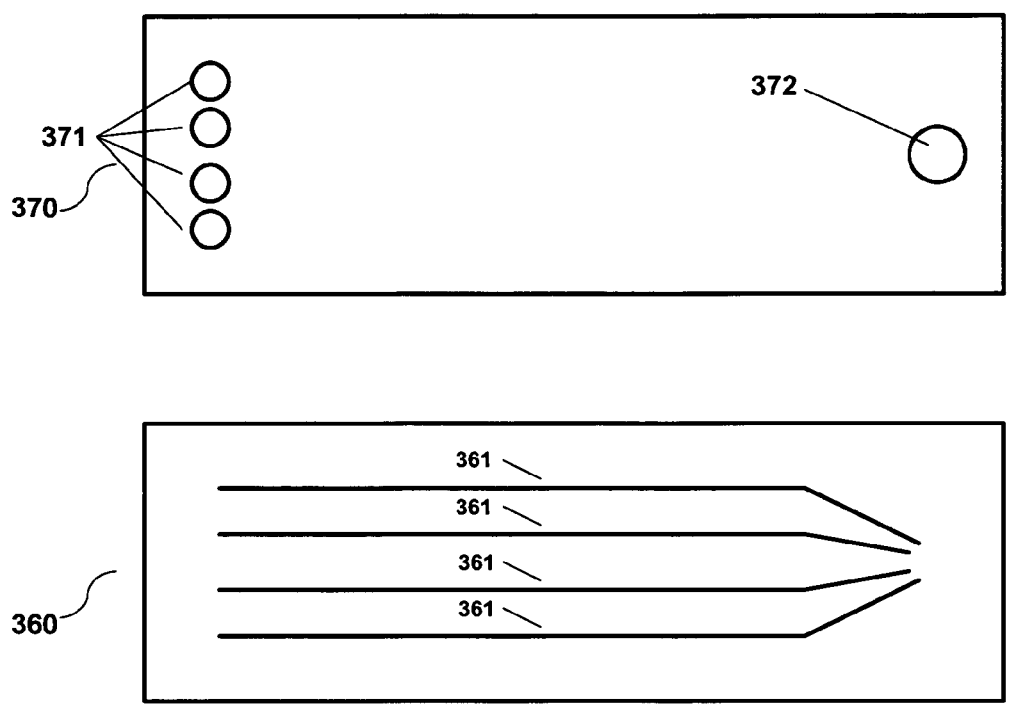
FIG. 3 illustrates separate device layers which can be used to construct a microfluidic separation and detection chip according to the various embodiments of the invention.

The chip (250) comprises of a substrate layer (360) and a cover layer (370) as shown in FIG. 3. A plurality of grooves (361) are patterned into the substrate layer. A series of vias (i.e., through holes) (371, 372) are formed in the cover layer to provide fluidic access to the microfluidic channels, and can be located at the ends of the microfluidic channels in the anode and cathode portions of the chip. Alternatively, vias can be formed in the substrate layer instead of the cover layers to achieve the same functionality. The top surface of the substrate layer is bonded with the bottom surface of the cover layer to form the microfluidic channels. Techniques for fabricating polymer-based microfluidic systems, reviewed extensively by Becker and Gartner (Becker, 2000, *Electrophoresis* 21: 12-26 and Becker, 2008, *Electrophoresis* 390(1): 89), which are hereby incorporated by reference in its entirety. Any number of these processes can be used to fabricate the plastic separation chip described herein.

In particular, the present plastic separation chips can be prepared by hot embossing of thin thermoplastic films with a master die of the negative of the structure to be produced. The master die can be prepared by using electroforming to replicate the device prepared in a solid substrate. The solid substrate can be glass sheets that are patterned by standard photolithographic and chemical etching methods known to those skilled in the art. The substrate and cover layers are diffusion bonded by the application of heat and pressure.

The substrate and cover layers of the chip can be constructed from a variety of plastic substrates including, but not limited to, polyethylene, poly(acrylates) (e.g., poly(methyl methacrylate)), poly(carbonate)s, and unsaturated, partially unsaturated or saturated cyclic olefin polymers (COP), or an unsaturated, partially unsaturated, or saturated cyclic olefin copolymers (COC) (e.g., ZEONOR™, ZEONEX™ or TOPAS™). In particular, COP and COC are advantageous for the present chip applications as they optically exhibit inherently lower autofluorescence in the visible wavelength range compared with other polymers.

The thickness of plastic substrate and cover layers utilized in the present process is kept thin to minimize autofluorescence from the chip. The plastic substrate and cover layers can each, independently, have a thickness of less than 2 mm, less than 1 mm, less than 750 µm, less than 650 µm, less than 500 µm, less than 400 µm, less than 300 µm, less than 200 µm, or less than 100 µm; or plastic substrate and cover layers can each, independently, comprise a plastic having a thickness ranging from 25-2000 µm, 25-1000, 25-750 µm, 25-650 mm, 25-500 µm, 25-400 µm, 25-300 µm, 25-200 µm, or 25-100 µm.

Figure 2:
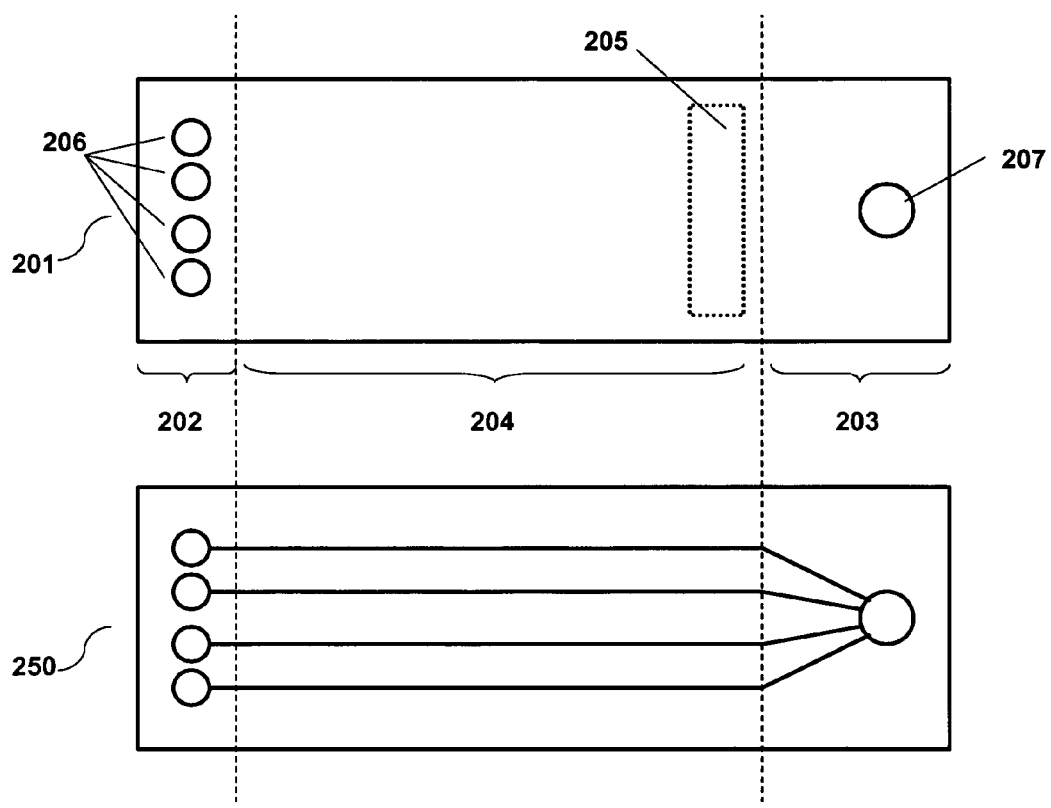
FIG. 2 illustrates separate support and chip layers which can be used to construct a microfluidic separation and detection chip according to the various embodiments of the invention.

In one embodiment, as exemplified in FIG. 2, the chip (250) is attached to a support (201) having a top and bottom surface, comprising an anode portion (202), a cathode portion (203), and a center portion (204) between the anode and cathode portions, wherein the center portion comprises a detection window (205), the anode portion comprises at least one anode well (206), and the cathode portion comprises at least one cathode well (207). The top surface of the chip, with the via holes up, is in contact with the bottom surface of the support, and the chip is fixedly attached to the support. The chip can be attached to the support according to methods known to those skilled in the art, for example, diffusion bonding, solvent bonding or adhesive bonding.

The support layer can be constructed from a variety of plastic substrates including, but not limited to, polyethylene, poly(acrylates) (e.g., poly(methyl methacrylate)), poly(carbonate)s, and unsaturated, partially unsaturated or saturated cyclic olefin polymers (COP), or an unsaturated, partially unsaturated, or saturated cyclic olefin copolymers (COC) (e.g., ZEONOR™, ZEONEX™ or TOPAS™). The thickness of a plastic support layers utilized in the present process is sufficiently thick in order to provide structural rigidity and to allow for sufficient volume of sample and buffers in the reservoirs. The thickness of the plastic support will range from 100-15,000 µm.

Alternatively, the chip can be fabricated by patterning the grooves on the solid support to form both the chip substrate and support structures together. A cover layer can be bonded to the support to complete the structure. In this configuration, the thickness of a detection window of the support and chip coincident with the detection portion of the microfluidic channels is kept thin to minimize autofluorescence. The thickness of this portion of the chip is less than 1000 µm, less than 750 µm, less than 500 µm or less than 250 µm; or ranging from 25-1000 µm, 25-750 µm, or 25-500 µm.

Each of the plurality of microfluidic channels can have a depth of at least 10 µm, 50 µm, 100 µm, 200 µm, 500 µm or 1 mm; or have a depth ranging from 1-1000 µm, 10-100 µm, 10-50, or 25-50 µm. The plurality of microfluidic channels can have a width of at least 25 µm, 50 µm, 100 µm, 200 µm, 500 µm or 1 mm; or have a width ranging from 25-1000 µm, 25-200 µm, or 50-200 µm. The microchannel cross-section of each channel can have a substantially square, rectangular, circular, semicircular, elliptical, triangular or trapezoidal cross-section. One skilled in the art will recognize that the microfluidic channels may or may not be uniform in depth, width and cross-section.

Each of the plurality of microfluidic channels (106) comprises a separation region (108) and a detection region (109). The separation region typically has channels with separation length of about 2-50 cm, 10-50 cm, 2-25 cm, 10-25 cm. The separation length is defined as the portion of the channel between the point of sample injection and the point of sample detection. The separation length is typically less than the total length of the separation channel which spans between the cathode and the anode reservoirs.

Simultaneous analysis of a plurality of samples can be performed by injecting and stacking each of the samples in a separate separation channel into any of the separation chips described herein. The application of an electric field along the separation channel causes the samples to migrate along the channel from the cathode portion toward the anode portion or the anode portion to the cathode portion of the separation channel, depending, for example, on the charges present on the surfaces of the channel (infra), as will be familiar to those skilled in the art. Migration of the sample through a sieving matrix separates species on the basis of size.

As the separated samples pass through the detection window dye labels attached to each species within the sample can be excited and the resulting fluorescence can be detected. The detection window typically overlaps the detection region of each of the plurality of microchannel at the termini of the separation region of each of the channels. Typically, the detection region for each of the plurality of microfluidic channels are in substantially the same location along the channels, such that the detection window can be in a single location in the center portion of the support.

An injector for simultaneously injecting a plurality samples into the plurality of sample or buffer wells is advantageously provided with the chip to enable simultaneous multiple sample separation and detection. Such injectors provide, for example, one sample of the plurality of samples to one microfluidic channel of the plurality of microfluidic channels. Injectors can introduce the samples to the channels according to any methods known to those skilled in the art, for example, by electrophoretic transport, pneumatic actuation or liquid actuation through a needle or tube or channel that connects the sample to the separation channel In certain embodiments, samples can be loaded into the chip through the cathode reservoirs of the chip. An injection volume of each sample can be introduced through one of the cathode wells according to methods known to those skilled in the art. For example, the sample can be injected via appropriate biasing of the separation channel and/or a cross-channel of the separation channel and the sample and waste wells such that a portion of the sample (i.e., the injection volume) in the sample well is provided to the separation channel. Following sample injection, additional buffer solution is introduced into each cathode well; sufficient volume can be provided to dilute any remaining sample in the well. For example, a volume of buffer is introduced into the cathode wells that is about at least 5, 10, 25, 50, or 100 times the injection volume of the sample. Alternatively, a volume of buffer is introduced into the cathode wells that ranges from about 5-100 times, 5-50 times, or 10-50 times the injection volume of the sample.

In other embodiments, each of the plurality of microfluidic channels further comprises an injection channel for introducing samples. For example, reference is made to FIG. 4; shown therein is an expanded view of a chip (400) showing the cathode portion (401) and adjoining section of the center portion (403). The cathode portion comprises at least one second via (405) and the center portion comprises a plurality of microfluidic channels (406). Each microfluidic channel further comprises, within the cathode portion of the chip, an injection channel (408) comprising a sample (409) and waste (410) well for each microfluidic channel.

Figure 4:
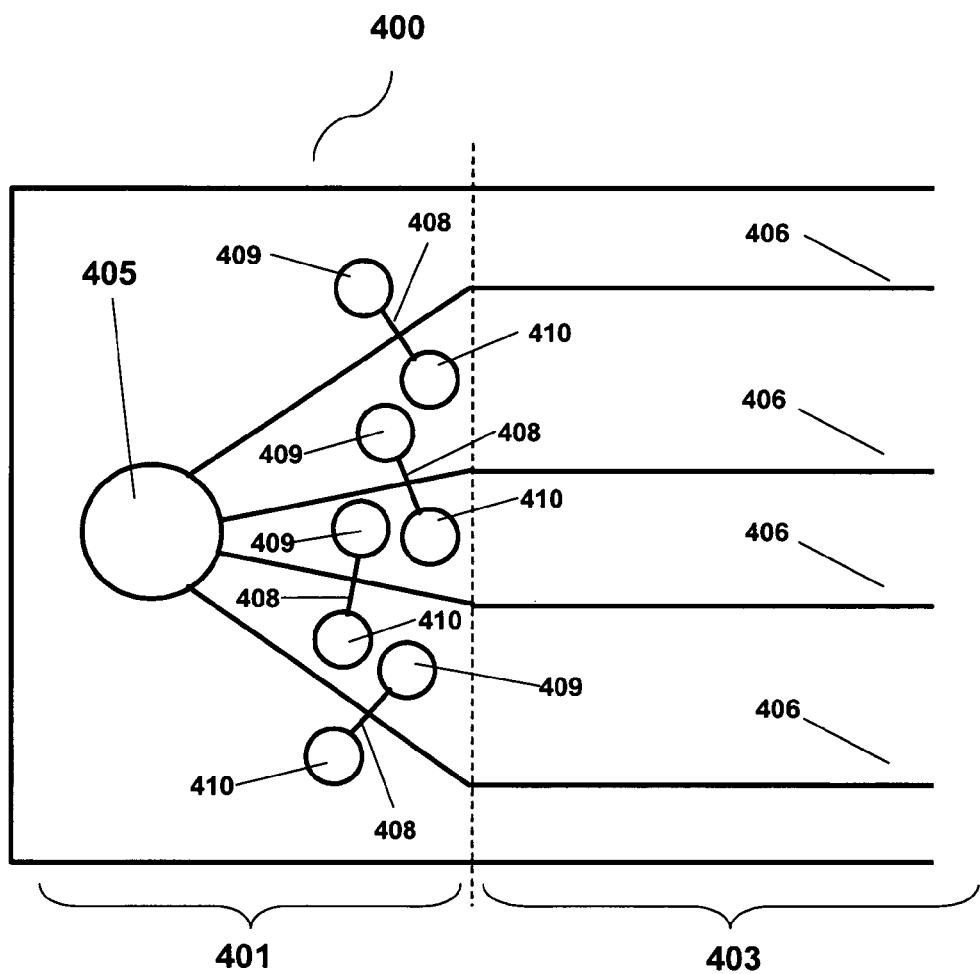
FIG. 4 illustrates an expanded view of the anode section of a microfluidic separation and detection chip according to the various embodiments of the invention.

The injection channel can be in a single cross-channel (as illustrated in FIG. 4), a single T-junction, or an offset double-T junction configuration. In some embodiments, the injection channel is an offset double-T junction configuration that minimizes the injection volume of sample, thereby improving separation resolution. Injection of a sample from the injection channel to the microfluidic channel can be accomplished according to methods known to those skilled in the art, including electrophoretic injection through application of the appropriate potentials at the sample, waste, anode and cathode wells.

Figure 5:
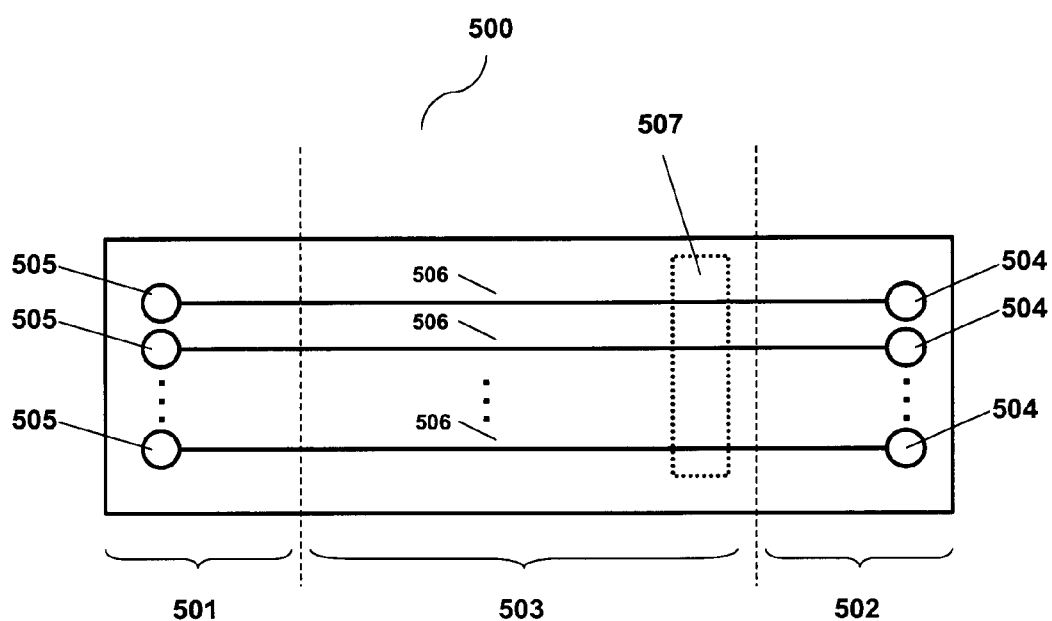
FIG. 5 illustrates a microfluidic separation and detection chip having injection channels according to the various embodiments of the invention

An alternative embodiment of the microfluidic separation and detection chip is illustrated in FIG. 5. The chip (500) comprises an anode portion (501), a cathode portion (502), and a center portion (503). The cathode portion comprises one first via (504) for each microfluidic channel (506) and the anode portion comprises at least one second via (505) for each microfluidic channel (506). The center portion comprises a plurality of microfluidic channels (506) and a detection window (507), each microfluidic channel having a separation region and a detection region; wherein each microfluidic channel is in fluid communication with one first via and one second via. The plurality of microfluidic channels are essentially in the same plane and do not intersect one another within the center portion. The detection window comprises a thin plastic and overlaps the detection region of each microfluidic channel.

In this instance, the injection channels are omitted in favor of an anode (second) and cathode (first) via for each microfluidic channel. An injection volume of each sample is introduced through one of the cathode via according to methods known to those skilled in the art (supra). Following sample injection, additional buffer solution is introduced into each cathode buffer well; sufficient volume is advantageously provided to dilute any remaining sample in the well, thereby mediating any background signal introduced from prolonged sample injection and improving the signal-to-noise ratio observed at the detection window. For example, a volume of buffer is introduced into the cathode wells that is about at least 5, 10, 25, 50, or 100 times the injection volume of the sample. Alternatively, a volume of buffer is introduced into the anode buffer wells that ranges from about 5-100 times, 5-50 times, or 10-50 times the injection volume of the sample.

Electrophoretic separation of the samples within the microfluidic channels is provided by the application of a potential difference across the microchannels on the microchip. A high voltage can be applied across the ends of the microchannels, typically by placing a cathode and anode in the cathode well and the anode well, respectively, establishing an electric field along the separation portion of the microfluidic channel, and moving the sample (e.g., nucleic acid) from the cathode end through the separation portion to the detection portion, and ultimately, to the anode. The electric field required for efficient separation often range from 50 V/cm to 600 V/cm. The voltage from the power supply is applied through electrodes and a buffer is used in the anode and cathode reservoir to provide electrical contact between the electrode and the sieving polymer.

High voltages required for sample separation are applied to the separation channel with electrodes that are in contact with the buffer that is in the cathode and anode wells. Due to the high voltages present at the electrodes that are in contact with the buffer, the buffer water molecules hydrolyze resulting in the formation of $OH^-$, $H^+$, and $H_2$ gas. This formation results in a change in the pH of the buffer with time, and formation of bubbles within the buffer. The pH change of the buffer can be attenuated through sufficient use of a buffer solution in the anode and cathode reservoirs (e.g., 1×TTE; Amresco) to provide contact between the electrode and the sieving matrix. The bubbles formed within the buffer have a tendency to migrate into the sieving matrix blocking the channel, resulting in poor separation of nucleic acids.

Bubbles that form at the electrode can be prevented from migrating into the channel by using one or a combination of the following methods. First, the electrode within the reservoir can be raised to move the source of bubble generation (electrode) away from the access holes in the channels. Secondly, a glass frit, polymer frit, or polymer membrane or polymer filter can be inserted between the cathode access hole and the end of the electrode. In particular, a polymer frit (e.g., polyetheretherketone, PEEK) can be inserted between the cathode access hole and the end of the electrode.

The frit, membrane, or filter is selected to be non-conducting and have a pore size that prevents bubbles formed at the electrode from passing through the pores. As a result of insertion of the frit, polymer membrane, or filter between the electrode and the sieving matrix, bubbles formed from the electrolysis process are prevented from entering the channels. This implementation can reduce and/or eliminate failures resulting from bubble blockage in the channels.

Separation devices for simultaneous analysis consisting of a plurality of samples are electrically connected so that a common power supply can be used to bias the plurality of channels simultaneously. Furthermore, physical constraints of the chip and instrument will usually not allow all the channels to have an identical physical layout with respect to length, depth and width.

To achieve substantially identical electrophoretic injection and separation conditions for each of the plurality of microfluidic channels, each channel segment of the individual devices should have essentially identical resistances and hence electric fields. A substantially identical electric field, that is wherein the electric fields across each of the plurality of microfluidic channels does not differ by more than about +/−5%, can be established by simultaneously adjusting both the length, width and depths of each of the plurality of microfluidic channels to adjust the resistance of each segment of the channels. The resistance, R, of each segment can be described by the following relationship:

$$R = \rho \frac{l}{A}$$

where $\rho$ is the resistivity, l is the length and A is the cross-sectional area of the channel.

Surface charges resident on the wall of the channels of the separation chip can result in electroosmosis and sample-to-wall interactions. These effects can be can minimized by applying a surface coating to the inner walls of the microfluidic channels. Such surface coatings and modifications can be accomplished through methods known to those skilled in the art (for example, Ludwig and Belder, 2003 *Electrophoresis* 24(15):2481-6).

A large number of candidates for surface modification are available including hydroxypropylmethylcellulose (HPMC), poly(ethylene oxide) (PEO), poly(vinyl alcohol) (PVA), polydimethyl acrylamide (PDMA), poly(vinylpyrrolidinone), dimethylacrylamide (DEA), diethylacrylamide (DEA), poly(diethylacrylamide) (PDEA), and mixtures thereof, such as PDMA:PDEA.

Additionally, for use in electrophoretic applications, each of the plurality of microfluidic channels is advantageously filled with a sieving matrix. Such sieving matrices can comprise, in non-limiting example, a linear polyacrylamide (PAA), polydimethylacrylamide (PDMA), polydiethylacrylamide (PDEA), polyvinylpyrrolydinone (PVP), and combinations thereof, including for example, PVP:PAA, PDMA:PAA, PDEA:PAA, PDEA:PDMA:PAA. In certain embodiments, the sieving matrix comprises 0.1-50 wt. % polyacrylamide. A number of these sieving matrices also possess dynamic self-coating capability. As practiced using these embodiments of the electrophoretic separation chips of the invention, nucleic acids move electrophoretically through a sieving matrix from the anode to the cathode end and are size-separated therein. As set forth above, the inner walls of the channels can be coated to minimize the influence of electroosmosis and nucleic acid-to-wall interactions.

Resolution, specifically herein electrophoretic resolution, is the ability to unambiguously discriminate two peaks separated in time (or by base size). The resolution (R) is defined by the following equation $$R = (2\ln 2)^{\frac{1}{2}} \frac{t_2 - t_1}{\Delta b(hw_1 + hw_2)}$$

where t is the migration time of the nth peak, hw is the full width and half-maximum of the nth peak, and $\Delta b$ is the base number difference between the two peaks. Single base pair resolution is defined at the point where R is greater than 0.4. Visually, two peaks are distinguishable from each other when the peak to valley ratio is greater than 0.7. Both R and peak-to-valley requirements must be met in order to have high resolution, and resolution can also be considered to be characteristic of a range of fragment sizes. The range of fragment sizes for alleles in STR analysis range from 90 to 400 bp and single basepair resolution across this range of fragment size is required for STR analysis. Fragment sizes for sequencing analysis range up to 1200 bp. The ability to achieve long read lengths and data throughput per lane is, in part, determined by the range over which the chip is able to generate single base-pair resolution.

The limit-of-detection for an optical detection system is defined by the signal to noise ratio (SNR). This ratio is defined as the ratio of a signal power to the noise power (standard deviation of noise power) corrupting the signal. A high SNR indicates a higher certainty that a signal is present. A signal-to-noise ratio of 3 is generally defined as that which is acceptable for confidently identifying the presence of a signal (Gilder, 2007, *J Forensic Sci.* 52(1): 97).

When analyzing and detecting a plurality of nucleic acid species in a nucleic acid sample, autofluorescence from the plastic in the detection window of the chip strongly contributes to the fluorescence background. An advantageous characteristic of the electrophoretic separation chips of the invention is that a thin detection window is used to minimize the background fluorescence from the plastic. This background level is compared to Borofloat®, which is a commonly-used substrate for fabricating microfluidic separation chips. With the use of a thin plastic window, a minimum of 1000 copies, 300 copies, 100 copies, 30 copies, 10 copies, 1 copy of template nucleic acid in the PCR process that generates fluorescently-labeled fragments for analysis can be detected. Also a minimum of 0.5 pmoles, 0.1 pmoles, 0.01 pmoles, or 0.001 pmoles of nucleic acid template for the sequencing reaction can be detected.

Separation and Detection Chip Applications

Applications of the various aspects of the invention extend broadly for both nucleic acid identification and sequencing. Examples of uses in human identification include criminal forensics and homeland security, for example identification at military checkpoints, borders and ports, airports and mass disaster sites. Veterinary identification applications including racehorse breeding and tracking, livestock breeding and pet identification also are within the scope of the uses of the disclosed electrophoretic chips.

Moreover, the instruments of this invention can be ruggedized, and thereby operated in the field where results can be used in real-time. As such, the instruments can be used at military checkpoints, borders and ports, airports, and mass casualty sites.

Applications of the technology to nucleic acid sequencing can be divided into four areas: human clinical diagnostics, including, for example, bacterial infections and antibody sensitivities, viral infections (identification and drug resistance profiling), genetic diseases, complex disorders (asthma, heart disease, diabetes) and pharmacogenomics; veterinary clinical diagnostics; research sequencing, including re-sequencing and finishing; biological weapons agent identification, including, for example, *B. anthracis* and Ebola virus detection; and food safety. Some examples follow.

A patient with HIV needs drug resistance testing. Today, it can take weeks to establish resistance. A drug resistant strain can take hold during that time. There is an unmet need for an instrument and system that can provide the answer within 1-2 hours, while the patient waits in the physician's office. Use of an electrophoretic separation chip according to the invention permits frequent drug-resistance monitoring, more clinically- and cost effective usage of anti-viral agents and better patient outcomes.

A patient with bacteremia is in shock. Today, it can take days to determine whether the causative agent is resistant to antibiotics and the identities thereof. In the interim, the patient must be treated with broad-spectrum antibiotics, which can cause serious side-effects to the patient and contributes to the increase in antibacterial resistance prevalent today. In addition, such treatments may be sub-optimal. Use of an electrophoretic separation chip according to the invention permits identification of the antibiotic resistance profile of the pathogen in 1-2 hours, leading to more effective, targeted treatment, reduction in antibiotic toxicities, and better patient outcomes. The benefits to the patient and to public health are complimentary.

A patient with cancer is undergoing surgery. Today, a tumor sample is taken to pathology while the patient is on the operating table. Based on the results of the simple histopathology strains, a decision is made concerning how aggressive the surgeon should be. Use of an electrophoretic separation chip according to the invention could replace histopathology with a definitive nucleic acid diagnosis of the cancer in less than an hour, allowing a better-informed surgical decision to be made.

The Examples which follow are illustrative of specific embodiments of the invention, and various uses thereof. They set forth for explanatory purposes only, and are not to be taken as limiting the invention.

EXAMPLES

Example 1

Chip Design and Electrophoresis

Example 1A

Chip Design

Figure 6:
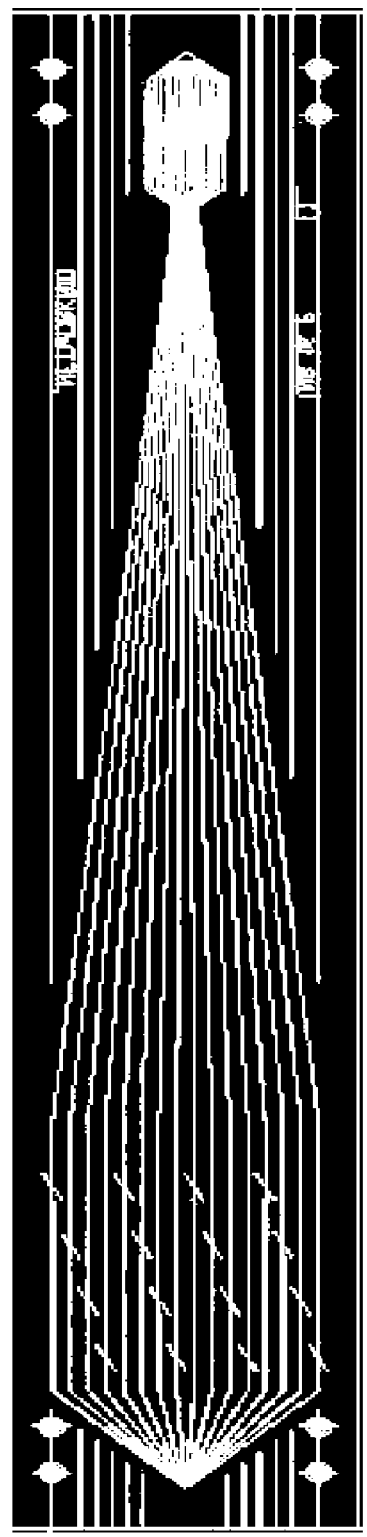
FIG. 6 is a schematic diagram of a microfluidic separation and detection chip according to the various embodiments of the invention.

A schematic diagram of a particular embodiment of the devices of the invention is illustrated in FIG. 6. This microfluidic device consisted of 16 microchannels, each with a double-T cross injector. The cross-sectional dimension of the channel (90 μm wide and 40 μm deep) and length of the channel between the anode and the cross-injector (25 cm) was equal for all channels. The separation lengths (distance between the intersection and the excitation/detection window) for each of the channels range from 16 to 20 cm long. The cross-sectional area of the channels between the cathode well and the injector was adjusted such that all the resistances and hence electric fields between the cathode and the intersection are essentially equal under bias. This ensured that the electric fields experienced by the samples were identical regardless of the separation channel into which a sample was loaded. The intersection voltages for all channels were essentially identical. The sample inlet and sample waste arms for sample injection were both 2.5 mm long. The offset between both channels was 500 μm.

Example 1B

Chip and Support Fabrication

Figure 7:
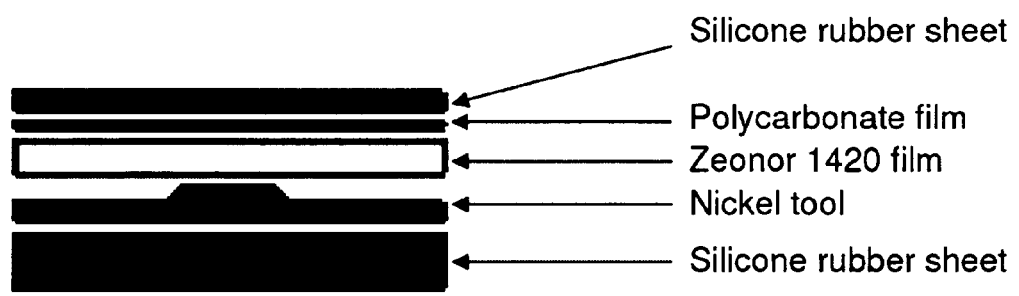
FIG. 7 illustrates the stack utilized for embossing.

The chip was patterned by hot-embossing, drilling to form access holes, and diffusion bonding to seal the channels. The master was fabricated in glass by photolithography, using a chemical wet etching process. This glass master was then used to fabricate a nickel-cobalt embossing tool by electroforming to generate a negative replicate of the glass master. Sheets of Zenor™-1420R film (5"×2" in size and 188 μm thick) were used as the substrate material. On these sheets, cathode, anode, sample and waste access holes were formed by drilling. This was followed by hot embossing the chip design features on the embossing tool into the substrate. Embossing was accomplished by placing the stack as illustrated in FIG. 7 in a heated hydraulic press for 15 minutes at 135° C. and 1250 psi of compressive pressure. The stack was held under 1250 psi of compressive pressure and allowed to cool to 38° C. prior to release. Fabrication of this chip with thin thermoplastic polymers containing norbornene monomers resulted in a low background fluorescence at excitation and detection window. Achieving high bond strength diffusion bonding allowed the use of high viscosity sieving matrices.

Diffusion bonding of the substrate was achieved by the aligning a sheet of Zenor™-1420R film (5"×2" in size and 188 μm thick) over the substrate and subjecting this stack to heat and pressure. No adhesive was applied between the sheets of film; bonding was accomplished entirely by heat and pressure. The final thickness of the chip was approximately 376 μm. Separation chips fabricated by this method were tested and demonstrated to be capable of withstanding at least 830 psi of pressure before failure.

Figure 8:
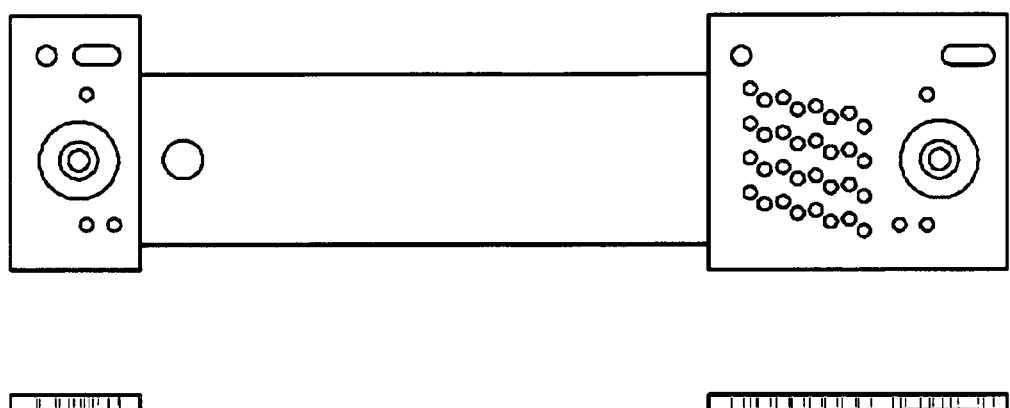
FIG. 8 illustrates a chip support that is fabricated by CNC milling from a ⅜" thick acrylic sheet (GE Plastic); (top) top view; bottom (side view).

FIG. 8 illustrates a chip support that was fabricated by CNC milling from a 3/8" thick acrylic sheet (GE Plastic). The chip support consisted of three main sections: the cathode board, the center part and the anode board. The cathode board contained the cathode well, sample and waste wells, and alignment holes. The anode board contained the anode well and alignment holes. Both the cathode board and the anode board were 3/8" thick to provide enough sample volume for sample injection and buffer volume for electrophoresis. The center portion was 0.04" thick and had an opening as the "detection window" for laser induced fluorescence detection in the microchannels. With this configuration, autofluorescence from the separation chip becomes dominated by the approximately 376 μm thick substrate. The separation chip was attached to the chip support with double-sided pressure sensitive adhesive. The adhesive was selected to be inert to the separation buffers and sieving matrices. The support and separation chip were attached with pressure sensitive epoxy. The thickness of the plastic in the excitation and detection area was minimized by fabricating a cut-out on the carrier in this region.

Figure 9:
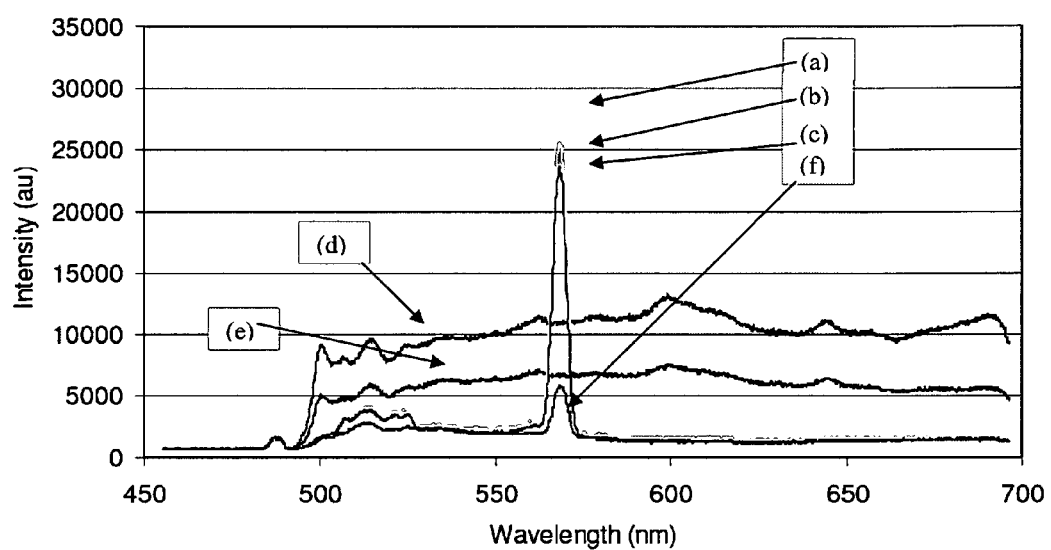
FIG. 9 is a fluorescence spectra demonstrating the low autofluorescence of the plastic chip compared to typical glass separation chips; (a) Assembled plastic chip (Pchip2); (b) Assembled plastic chip (Pchip1); (c) plastic cover layer only; (d) glass chip, 1.4 mm thick; (e) glass chip 0.7 mm thick; (f) plastic substrate only.

The optical emission spectrum of Zenor™-1420R has the Raman emission peak at 570 nm which has limited fluorescence detection with fluorescent dyes. FIG. 9 demonstrates low autofluorescence of the plastic chip (PChip1 and PChp2) compared with typical glass separation chips (Glass 1.4 mm and Glass 0.7 mm). The low autofluorescence of the plastic chip was achieved by selecting a COP polymer and minimizing the thickness of the device in the detection area and by fabricating the device with thin films.

Example 1C

Surface Modification and Sieving Matrix

Surface modification was accomplished by initially pretreating microchannel surfaces with de-ionized water, followed by 1 M NaOH. A nitrogen flush was applied to remove fluids from the channels. Treatment of the surface was followed by flowing 0.1% (w/v) hydroxypropylmethylcellulose (HPMC) solution through the channels followed by incubation overnight at room temperature. High purity nitrogen was used to flush through the channels to remove fluids inside the channel.

The sieving matrix used for these experiments was 4% linear polyacrylamide (LPA) in 7M Urea and 1×TTE (Amresco) buffer Example 1D Electrophoresis STR Sizing Electrophoretic separation and analysis of nucleic acid analysis was performed on the Genebench-FX™ Series 100 (Network Biosystems, Inc., Woburn, Mass.). This instrument was configured to accept the plastic separation chip and chip support to allow for good optical, electrical and thermal coupling between chip and instrument. The temperature of the chamber was maintained at 50° C. throughout the operation.

For DNA sizing experiments human genomic DNA was amplified with the ABI AmpFlSTR kit (Applied Biosystems Inc., Foster City, Calif.). PCR product (2.7 μL) was mixed with 0.3 μL of sizing standard and 10 μL of formamide, and loaded into the sample wells for analysis. The assay consisted of pre-electrophoresis performed at 156 V/cm for 6 minutes prior to sample introduction by applying a potential difference of 3900 V at the anode well and grounding the cathode well. DNA samples were introduced by applying an electric field of 350 V/cm for 18 seconds, followed by a dual load of 1.2 minute by applying an electric field of 350 V/cm across the sample and waste wells and simultaneously applying an electric field of 15.6 V/cm across the cathode and anode wells. After sample injection, electrophoretic DNA separation was performed by applying an electric field of 156 V/cm across the cathode and anode well while maintaining a pullback voltage of 800 V for 40 minutes.

For DNA sequencing experiments, M13 plasmid was cycle-sequenced with the GE Amersham DYEnamic™ ET dye terminator cycle sequencing kit (GE Healthcare), ethanol precipitated and resuspended in 10 μL deionized water. The separation assay consisted of a pre-electrophoresis performed at 156 V/cm for 6 minutes prior to sample introduction by applying a potential difference of 3900 V at the anode well and grounding the cathode well. DNA sample was introduced by applying an electric field of 350 V/cm for 60 seconds. After sample injection, electrophoretic DNA separation was performed by applying an electric field of 156 V/cm across the cathode and anode well while maintaining a pullback voltage of 400 V for 60 minutes. DNA separation resolution was calculated by extracting the peak information (peak spacing and peak width) from Peakfit®.

Figure 10:
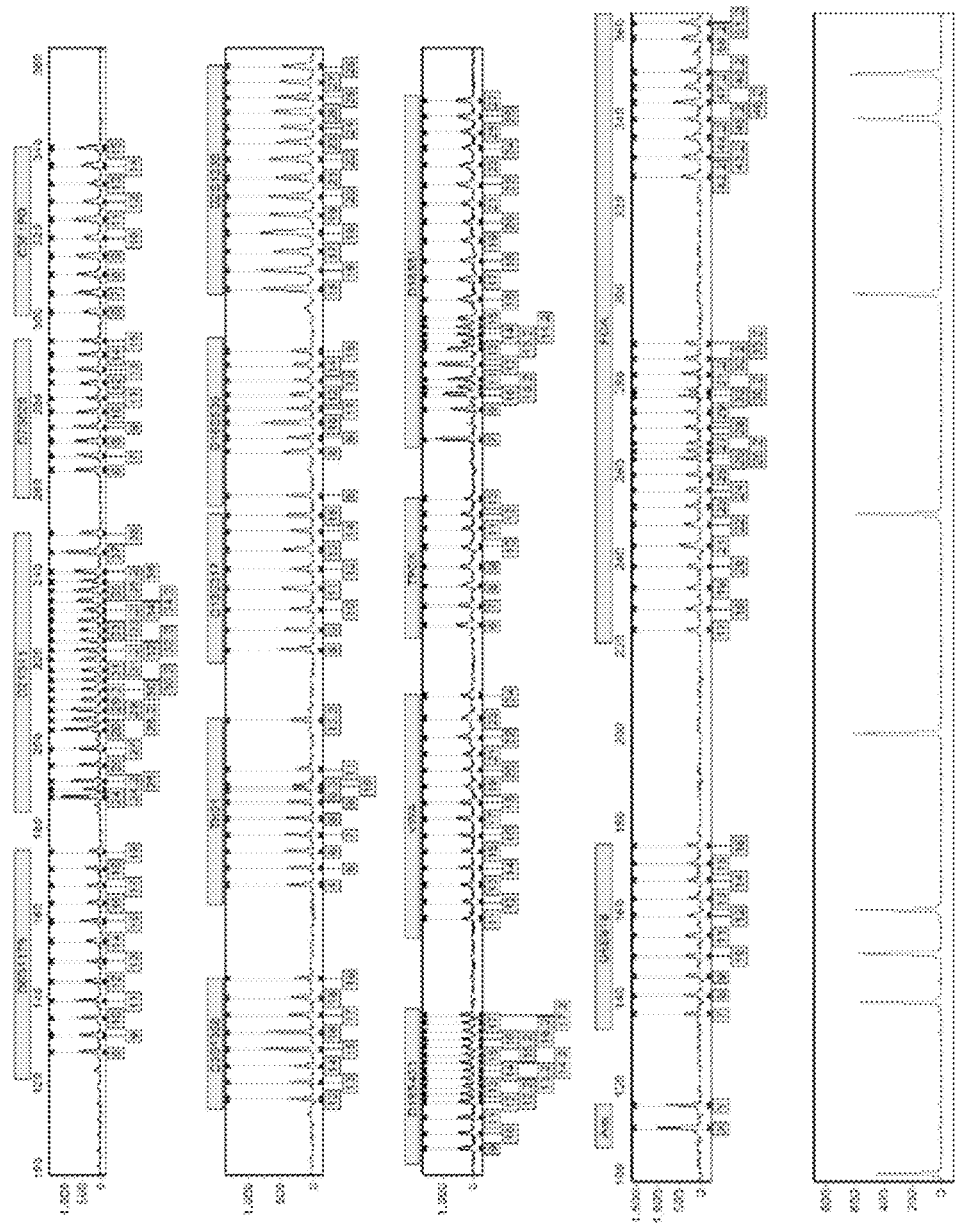
FIG. 10 is an allele-called profile for the allelic ladder from a 5-color labeled kit (ABI AmpFlSTR Identifiler kit); top to bottom: blue, green, yellow, red, orange detector signals.
Figure 11:
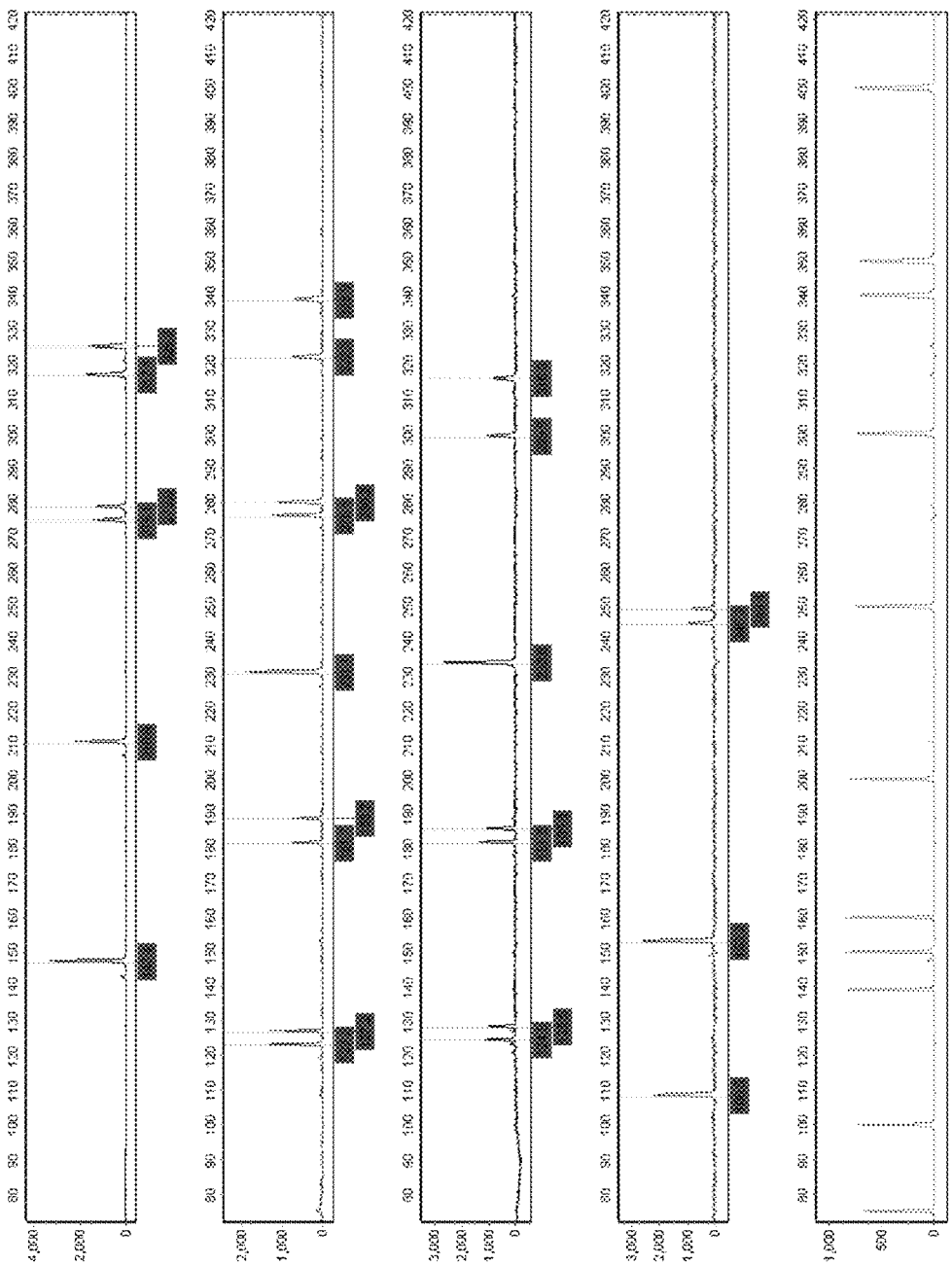
FIG. 11 is an allele-called STR profile for 9947A human genomic DNA, top to bottom: blue, green, yellow, red, orange detector signals; full profile is achieved at 1.0 ng of DNA template.
Figure 12:
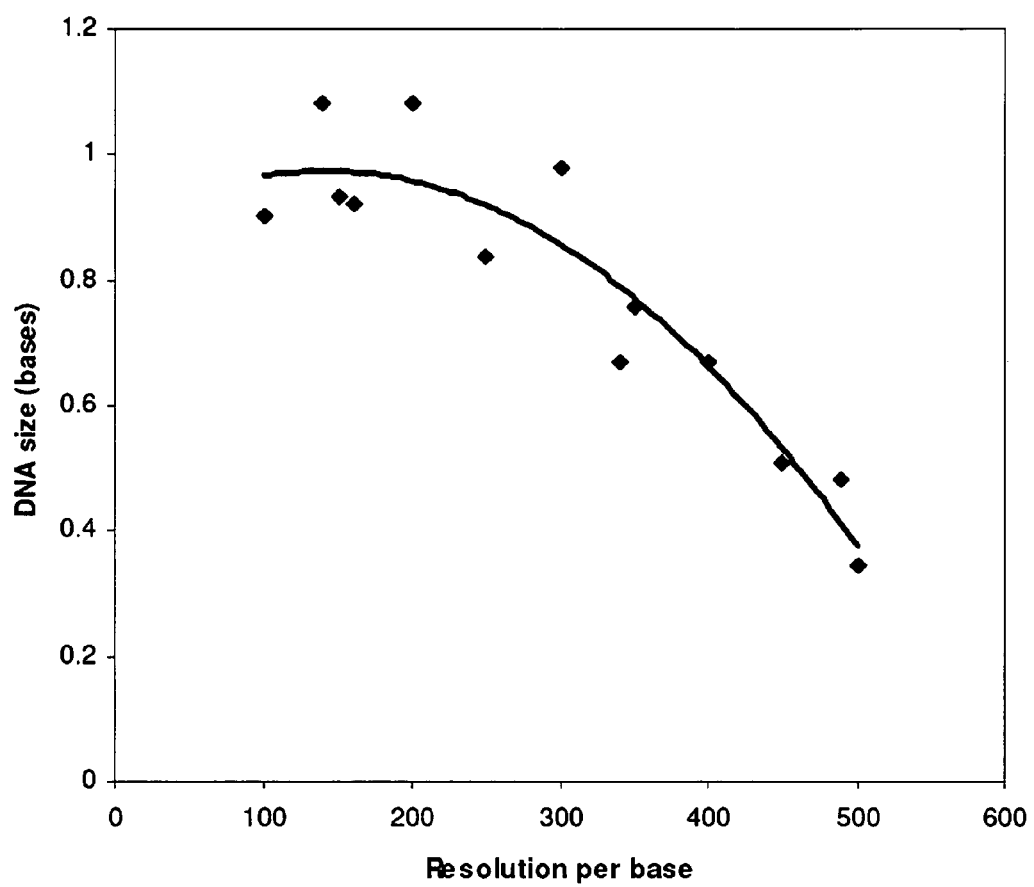
FIG. 12 shows the resolution with R>0.4 for to 480 bp, demonstrating that single base resolution to 480 bp; top to bottom: blue, green, yellow, red, orange detector signals.
Figure 13:
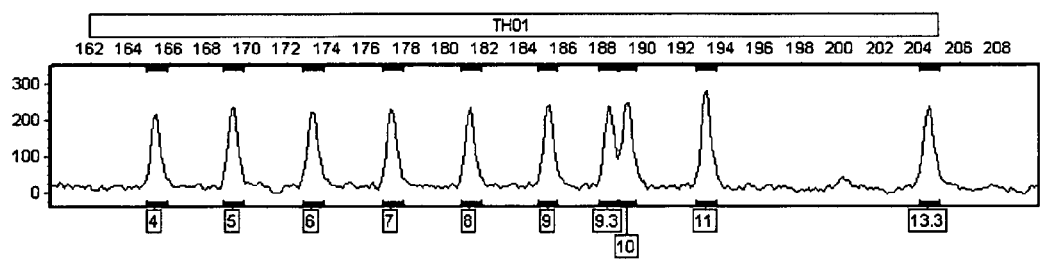
FIG. 13 shows the resolution of 2 alleles (THO1 9.3 and 10) that are separated by 1 nucleotide.
Figure 14:
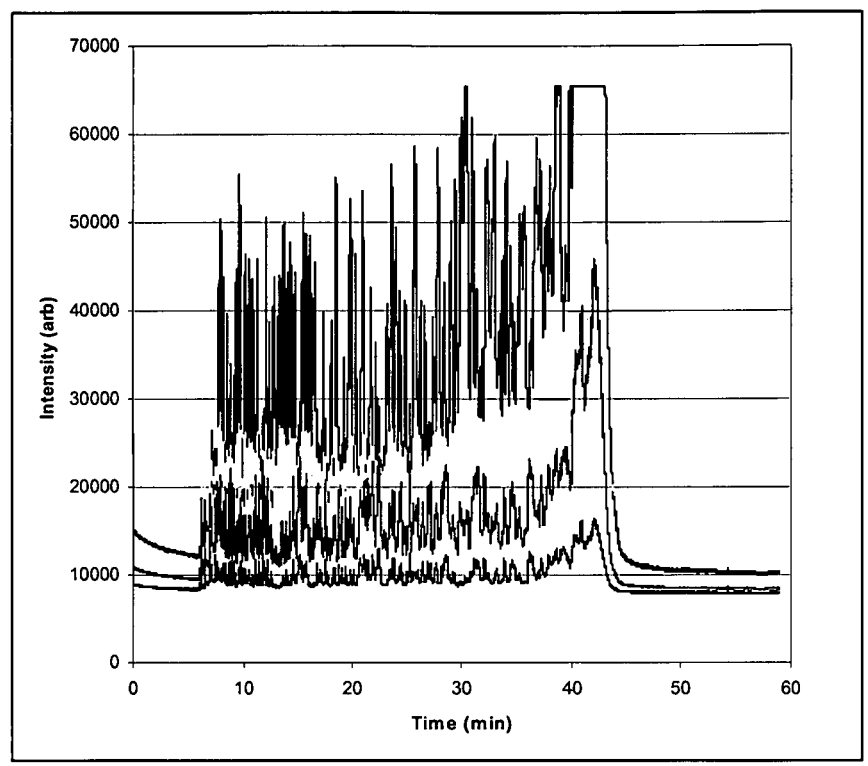
FIG. 14 is a DNA sequencing analysis of pGEM fragment; top to bottom: blue, green, yellow, and red detector signals.
Figure 15:
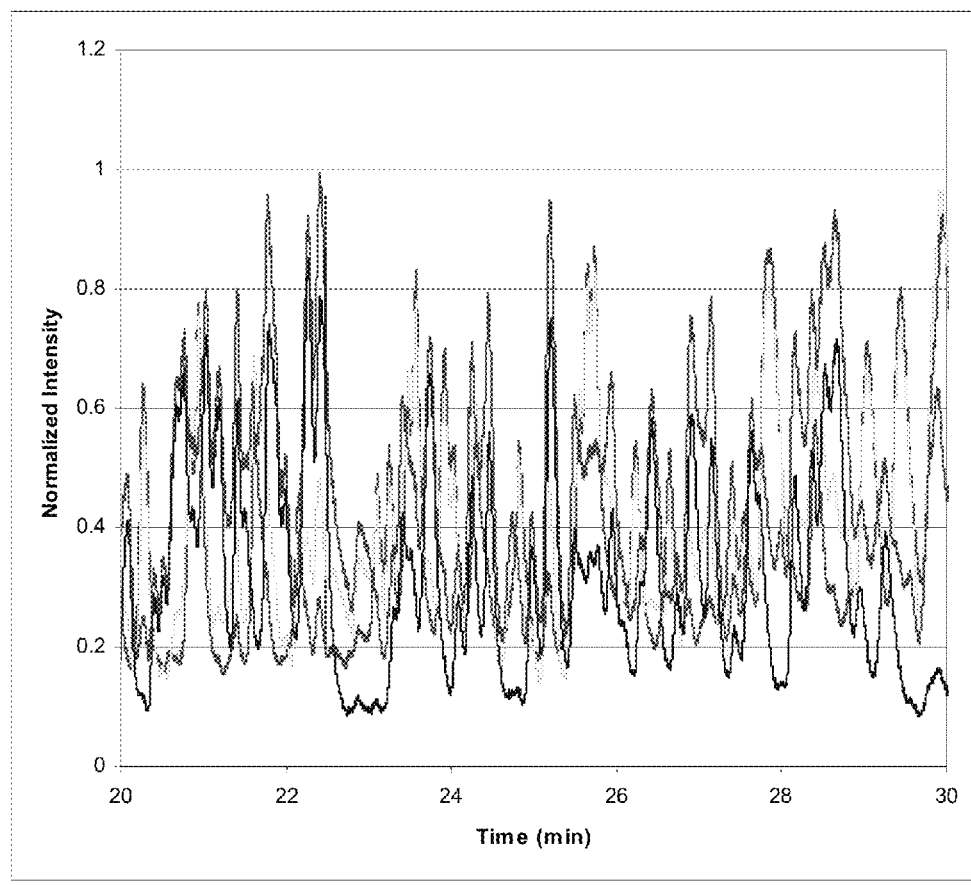
FIG. 15 is a composite four base-pair graph showing a DNA sequencing analysis of a pGEM fragment.

Successful separation was achieved simultaneously in 16 lanes in the plastic chip. FIG. 10 shows allele called profile for the allelic ladder from a 5-color labeled kit (ABI AmpFlSTR Identifiler kit). These results demonstrated that devices of the invention were able to separate with 5 colors in a plastic chip and clearly resolve alleles including ones that are spaced by a distance equivalent to only a single base pair (THO 1, allele 9.3 and 10). FIG. 11 shows an allele called STR profile for 9947A human genomic DNA, showing that a full profile was achieved at 1.0 ng of DNA template. FIG. 12 shows the resolution with R>0.4 for up to 480 bp, demonstrating single-base resolution up to 480 bp. FIG. 13 illustrates this resolution by showing 2 alleles that are spaced by 1 nucleotide can be clearly resolved with no ambiguity. FIGS. 14 and 15 shows a DNA sequencing profile demonstrating single basepair resolution.

Example 2

Electrokinetic Injection Plastic Chip

Example 2A

Chip Design

Another configuration of the electrophoretic separation chips of the invention uses a single channel for separation.

Figure 16:
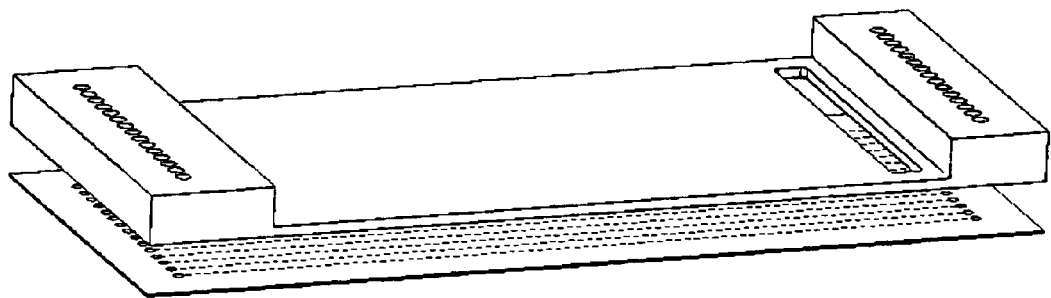
FIG. 16 is a breakaway schematic diagram of a chip design for direct electrokinetic sample injection showing the support (upper) and chip (bottom) layers.

Each sample is introduced into a separation channel by electrokinetic sample injection. This alternative approach allows for the use of small sample volumes and a significant simplification in the separation process. A schematic diagram of chip design for electrokinetic sample injection is shown in a breakaway view in FIG. 16, showing the support and separation chip sections. The device consists of 16 microchannels that are effectively 20 cm in separation length. Each channel has an access hole at each end. The channels are 90 μm wide and 40 μm deep.

Example 2B

Device Fabrication

The device of FIG. 16 is fabricated following the procedure described in the section above. In summary, access holes (1 mm in diameter) are formed in a COP film (Zeonor™-1420R) with a thickness of 188 μm. Channel patterns (width 90 μm and depth 40 μm) are then formed by hot embossing. A cover of COP (Zeonor™-1420R) is diffusion bonded to the substrate to seal the channels.

Example 2C

Electrophoresis

The device is prepared for separation by applying a surface modification to the channels as described in the section above. This is followed by filling the channels with a sieving matrix. Samples are loaded into the sample/cathode reservoir. An injection field is applied through the electrodes to the sample to inject negatively charged DNA into the separation channel. Following injection of DNA into the channels, buffer (1×TTE; Ameresco) is added to the sample/cathode reservoir at a volume 10 times the volume of the sample. An electric field is applied across the cathode and anode to separate the DNA from the injection plug down the separation channel. The addition serves to dilute the sample that is in the sample/cathode and there is no need to remove the sample prior to loading the buffer. Separation and detection is performed on a Genebench-FX™ Series 100 instrument, and data analysis is performed with the software described in the previous examples.

Example 3

DNA Sequencing

For DNA sequencing analysis, DNA template is amplified in a reaction mix consisting of PCR enzyme SpeedSTAR HS (Takara, Madison, Wis.) (U/μL): 0.025, Fast Buffer 1: 1×, dNTPs: 0.25 mM, Primer (forward): 250n M, and Primer (reverse): 250 nM. A desired level of template DNA is added to the mix. DI water or TE buffer (Tris 10 mM or EDTA 0.1 mM) is added to the reaction mix to a total volume of 10 μL. Thermal cycling of the PCR reaction mix, following manufacturer's recommended protocols, consists of hot start activation of 60 seconds at 95° C., 30 cycles of denaturation, anneal and extension (5 seconds at 98° C., 10-15 seconds at 55° C. and 5-10 seconds/kbp at 72° C.) and a final extension of 60 seconds at 72° C.

The entire PCR product is cleaned up by using a 30K MWCO UF filter (Pall, East Hills, N.Y.), following manufacturers protocol. The cleaned up product, with consisting of DNA in DI water, is either diluted or applied in its entirety as template for the sequencing reaction.

Cycle sequencing of PCR template, was performed using the DYEnamic™ ET Terminator Cycle Sequencing Kit (GE Amersham Biosciences) at half strength reaction with the following reaction mix. Sequencing Premix: 4 μL, Dilution Buffer: 4 μL, Primer (101M): 5 pmol. DNA template was added to the sequencing reaction mix. DI water was added to the reaction mix to a total volume of 20 μL. Following manufacturer's recommended cycling protocols the cycling condition used consists of thirty cycles of (20 seconds at 95° C., 15 seconds at 50° C., 60 seconds at 60° C.).

The sequencing reaction mix is cleaned up by ethanol precipitation. The precipitated product is resuspended in 13 μL of DI water and used as sample for separation and detection.

For STR analysis, amplification is carried out in 10 μL reactions with the following reaction mix consisting of: PCR enzyme SpeedSTAR HS (Takara, Madison, Wis.) (U/μL): 0.0315, Fast Buffer 1: 1×, Primer set: 2 μl, Fast Buffer 1: 1×, dNTPs: 200 μM, Primer (forward/Reverse): 2 μL from AmpFlSTR Profiler™, COFiler™ or Identifiler™ (Applied Biosystems, Foster City, Calif.).

The cycling protocol follows enzyme manufacturers conditions consisting of a hot start activation of 60 seconds at 95° C. followed by 28 cycles of denaturation, anneal and extension (4 at 98° C., 15 s at 59° C., 5 s at 72° C.) and a final extension of 60 seconds at 72° C. PCR product is used as sample for separation and detection. Alternatively, the PCR product can also be purified and used as sample for separation and detection.

It should be understood that the foregoing disclosure emphasizes certain specific embodiments of the invention and that all modifications or alternatives equivalent thereto are within the spirit and scope of the invention as set forth in the appended claims.

We claim:

1. A plastic electrophoresis chip for separation and detection of DNA fragments comprising:
    a substrate having top and bottom surfaces, further comprising an anode portion, a cathode portion, and a center portion between the anode and cathode portions, and
    a cover layer having top and bottom surfaces such that the top surface of said substrate layer is bonded with the bottom surface of said cover layer to form a plurality of non-intersecting microfluidic channels and a detection window, each nonintersecting microfluidic channel having an equivalent length of between 2-50 cm and a separation and detection region; and the length, widths and depths of each of the plurality of microfluidic channels is adjusted so that the resistances in each of the plurality of microfluidic channels is substantially equivalent and configured to detect DNA; and wherein,
    each non-intersecting microfluidic channel is in fluid communication with a first via located at said anode and a second via located at said cathode, said detection window comprised of plastic selected from the group consisting of polyethylene, a poly(carbonate), an unsaturated, partially unsaturated or saturated cyclic olefin polymer (COP), an unsaturated, partially unsaturated, or saturated cyclic olefin copolymer (COC), or a norbornene thermopolymer, and said detection window has a thickness of less than 2 mm, and overlaps in the detection region of each of said plurality of microfluidic channels.

2. The chip of claim 1 wherein the detection window plastic has a thickness of less than about 300 μm.

3. The chip of claim 1 wherein the detection window plastic has a thickness of less than about 500 μm.

4. The chip of claim 1 wherein the detection window plastic has a thickness of one millimeter or less.

5. The chip of claim 1, wherein each of the plurality of microfluidic channels further comprises an injection channel.

6. The chip of claim 1 wherein the thin plastic is selected on the basis that it essentially does not fluoresce light having a wavelength between 500 and 800 nm when excited at a wavelength of about 488 nm.

7. The chip of claim 1, wherein a plurality of nucleic acid species in a nucleic acid sample generated for fragment sizing applications can be detected with a starting with a single copy of a nucleic acid template for PCR amplification.

8. The chip of claim 1, wherein a plurality of nucleic acid species in a nucleic acid sample generated for DNA sequencing application can be detected with starting with a single copy of a DNA template for PCR amplification.

9. The chip of claim 1 wherein each of the plurality of microfluidic channels further comprises a surface coating.

10. The chip of claim 9 wherein the surface coating is hydroxypropylmethylcellulose (HPMA), poly(ethylene oxide) (PEO), poly(vinyl alcohol) (PVA), poly(dimethyl acrylamide) (PDMA), poly(vinylpyrrolidinone), dimethylacrylamide (DMA), diethylacrylamide DEA, poly(diethylacrylamide) and mixtures thereof.

11. The chip of claim 9 wherein the each of the plurality of microfluidic channels further comprises a sieving matrix.

12. The chip of claim 11 wherein the sieving matrix comprises a linear or cross-linked poly (N,N-dialkylacrylamide), linear polyacrylamide, polydimethylacrylamide, polyvinylpyrrolydinone, or combinations thereof.

13. The chip of claim 12 wherein the sieving matrix comprises 1-50 wt % polyacrylamide.

14. The chip of claim 1 further comprising a porous layer between each cathode well and each microfluidic channel, wherein the porous layer is capable of substantially blocking passage of gas bubbles from the cathode wells into each microfluidic channel.

15. The chip of claim 14 wherein the porous layer comprises a glass frit, a polymer frit, a polymer membrane, or a polymer filter.

16. The chip of claim 1, wherein each of the plurality of microfluidic channels further comprises an injector for simultaneously injecting a plurality of samples to be analyzed, one sample into each of the plurality of microfluidic channels.

17. An apparatus comprising
a support comprising a second detection window; and
a chip according to claim 1, wherein the chip is attached to the support and wherein the second detection window coincides with the detection window of the chip.

18. A method for electrophoretically separating and detecting a plurality of samples simultaneously comprising,
providing a plurality of samples into each of a plurality of microfluidic channels on a microchip according to claim 1;
applying an electric potential across the plurality of microfluidic channels to separate detectable species comprising each of the plurality of analysis samples;
detecting each of the detectable species comprising the plurality of separated samples at the detection window.

19. The method of claim 18, further comprising the step of maintaining a substantially identical electric field across each of the plurality of microfluidic channels.

20. The method of claim 19, wherein an essentially identical electric field is maintained across each of the plurality of microfluidic channels by balancing the resistance of each portion of each of the plurality of microfluidic channels.

21. The method of claim 18, wherein the detectable species comprise nucleic acids.

22. The method of claim 21, wherein the detectable species comprise dyes functionally attached to the nucleic acids.

23. The chip of claim 1, wherein the first via and the second via are comprised within the cover layer.

24. The apparatus of claim 17, wherein the first via and the second via are comprised within the cover layer.

25. The chip of claim 1, wherein the detection window plastic has a thickness between about 25 and 2000 μm.

* * * * *